US012680998B2

(12) United States Patent
Morawek et al.

(10) Patent No.: US 12,680,998 B2
(45) Date of Patent: Jul. 14, 2026

(54) METHOD FOR THE ENERGY-SAVING, CONTINUOUS MEASURING OF A QUALITY OF A LIQUID AND MEASURING DEVICE FOR CARRYING OUT THE METHOD

(71) Applicant: s::can GmbH, Vienna (AT)

(72) Inventors: Roman Morawek, Vienna (AT); Christian Haselberger, Vienna (AT)

(73) Assignee: S::CAN GMBH, Vienna (AT)

( * ) Notice: Subject to any disclaimer, the term of this patent is extended or adjusted under 35 U.S.C. 154(b) by 309 days.

(21) Appl. No.: 18/569,572

(22) PCT Filed: Jan. 31, 2023

(86) PCT No.: PCT/EP2023/052219
§ 371 (c)(1),
(2) Date: Dec. 12, 2023

(87) PCT Pub. No.: WO2023/148130
PCT Pub. Date: Aug. 10, 2023

(65) Prior Publication Data
US 2024/0280555 A1      Aug. 22, 2024

(30) Foreign Application Priority Data
Feb. 1, 2022      (EP) ..................................... 22154550

(51) Int. Cl.
*G01N 33/18* (2006.01)
*G01N 31/22* (2006.01)

(52) U.S. Cl.
CPC ....... *G01N 33/1886* (2013.01); *G01N 31/221* (2013.01)

(58) Field of Classification Search
CPC .... G01N 33/00; G01N 33/18; G01N 33/1886; G01N 31/221
See application file for complete search history.

(56) References Cited

U.S. PATENT DOCUMENTS 4,464,230 A      8/1984   Langdon
7,007,541 B2 *   3/2006   Henry ................ G01N 33/1886
                                                                73/19.1

(Continued)

FOREIGN PATENT DOCUMENTS

AT            520515 A1      4/2019
EP          3194908 B1      1/2021
JP        S59162444 A      9/1984

OTHER PUBLICATIONS

ISA European Patent Office, International Search Report Issued in Application No. PCT/EP2023/052219, Feb. 14, 2023, WIPO, 4 pages.

*Primary Examiner* — Nguyen Q. Ha
(74) *Attorney, Agent, or Firm* — McCoy Russell LLP

(57) ABSTRACT

Measuring device and method for energy-saving, continuous measuring of a quality of a liquid using a measuring device having a sensor for detecting a measurement variable in the liquid, wherein: the sensor is alternatingly activated for a duration of a switch-on phase and deactivated for a duration of a switch-off phase; during a defined switch-on phase, the sensor detects the measurement value as a comparison measurement value representing a measured quality of the liquid; a reference measurement is carried out to detect a reference measurement value representing a reference quality of the liquid; during further switch-on phases, the sensor continuously detects measurement values in the liquid as operating measurement values representing operating qualities of the liquid; and a final measurement value representing a final quality of the liquid is determined by a calculation rule based on the comparison measurement value, the reference measurement value and the operating measurement values.

14 Claims, 2 Drawing Sheets

(56) References Cited

U.S. PATENT DOCUMENTS

| | | |
|---|---|---|
| 2009/0068754 A1 | 3/2009 | Wu et al. |
| 2020/0225205 A1 | 7/2020 | Weingartner et al. |
| 2020/0340968 A1 | 10/2020 | Zakinov |

* cited by examiner

METHOD FOR THE ENERGY-SAVING, CONTINUOUS MEASURING OF A QUALITY OF A LIQUID AND MEASURING DEVICE FOR CARRYING OUT THE METHOD

CROSS REFERENCE TO RELATED APPLICATIONS

The present application is a U.S. National Phase of International Application No. PCT/EP2023/052219 entitled "METHOD FOR THE ENERGY-SAVING, CONTINU-OUS MEASURING OF A QUALITY OF A FLUID AND MEASURING DEVICE FOR CARRYING OUT THE METHOD," and filed on Jan. 31, 2023. International Application No. PCT/EP2023/052219 claims priority to European Patent Application No. 22154550.2 filed on Feb. 1, 2022. The entire contents of each of the above-listed applications are hereby incorporated by reference for all purposes.

TECHNICAL FIELD

The invention relates to a method for the energy-saving, continuous measuring of a quality of a liquid, in particular water, using a sensor for detecting a measurement variable.

BACKGROUND AND SUMMARY

Furthermore, the invention relates to a measuring device for the energy-saving continuous measuring of a quality of a liquid, in particular water, using a sensor.

As is known, the quality of a liquid, for example, water, is detected with sensors, wherein the sensors are supplied with electric power. If no external power supply is perma-nently available for this purpose, the energy for the sensors is provided by means of electric power storage means, e.g. batteries, in particular rechargeable batteries. Such electric power storage means are renewed or recharged in the course of maintenance activities, but this is associated with a corresponding maintenance effort. Therefore, it is desirable to maintain a charged state of the energy storage means for as long as possible, i.e. to operate the sensors as energy-saving as possible. This is often achieved by an extended measurement interval, i.e. by longer time intervals between successive measurements with the sensor. Between mea-surements, the sensor is deactivated and a controller for the sensor is put into an idle or sleep state. After a defined time has elapsed, the controller leaves the idle state and activates the sensor for a short time to perform the measurement.

While such an energy-saving operation is quite expedient for some sensors, other sensors for measuring a quality of a liquid, in particular water, require a substantially continuous power supply, but at least a comparatively substantially longer power supply, for example of several hours, in order to provide correct measurement results. If these other sen-sors were powered for several hours to obtain a single measurement result, and then deactivated to save energy, only a few measurement results per day would be obtained with these other sensors. However, such a low measurement rate is often inadequate for measuring a quality of a liquid, in particular water.

As stated in AT 520515 A1, sensors for measuring the water quality are sometimes also connected to pumps, which ensure the water transport to the sensor. In such systems, the associated pump must therefore also be activated in addition to the sensor itself in order to carry out measurements, which further increases the overall energy requirement. Apart from a short lead time to ensure water exchange before sensor activation, in the de-energised phase of the sensor, the pump can also be de-energised, which further increases energy savings.

EP 3 194 908 B1 relates to monitoring systems, for example for pipeline or pipe networks. The monitoring system can comprise a wireless telemetry unit connected to at least one threshold value indicator for detecting a liquid level and to at least one sensor for determining a state of the liquid in a conduit of the pipe network. The telemetry unit can supply power to the sensor when the threshold value indicator indicates a liquid level above a threshold value. Similarly, the telemetry unit can interrupt power to the sensor when the threshold value indicator indicates a liquid level below the threshold value. In this way, power con-sumption by the sensor is reduced. The document already mentions that once the sensor is supplied with power, it needs a certain amount of time to warm up. Details of the warm-up phase or solutions to bypass the warm-up time are not given.

US 2020/0340968 A1 relates to a device for monitoring parameters of liquids, such as water quality, in an energy-saving manner. The device comprises, for example, a chlo-rine sensor and a controller that controls the operation of the device at least between a switched-off mode, an active mode in which the device performs measurements, and an idle mode in which no measurements are performed and the controller and the chlorine sensor are only minimally sup-plied with power, so that the chlorine sensor does not go into a passive mode and does not need to be recalibrated. The low energy required for this can be taken from batteries. US 2020/0340968 A1 thus describes an energy-saving operation of a chlorine sensor, but not a switching off of the sensor between successive measurements and how associated mea-surement inaccuracies are prevented.

The object of the invention is to provide a method and a measuring device of the type mentioned at the outset, which enable an energy-saving continuous measurement of a qual-ity of a liquid, in particular water, with a sensor. In particular, the sensor is intended to be operated with lower power consumption compared to normal operation, yet measure-ment results are obtained with essentially the same accuracy as in the case of normal operation with higher power consumption.

For this purpose, the invention provides a method and a measuring device. Advantageous embodiments and further developments are given in the dependent claims.

The object is solved according to the invention by means of a method for the energy-saving, continuous measuring of a quality of a liquid, in particular water, using a sensor for detecting a measurement variable, wherein:

S1) the sensor is provided as part of a measuring device for measuring the quality of a liquid and the measuring device is arranged relative to the liquid;

S2) the sensor is alternately activated for the duration of a switch-on phase and deactivated for the duration of a switch-off phase;

S3) a measurement value is detected as a comparison measurement value using the sensor during a defined switch-on phase; for which defined switch-on phase the comparison measurement value differs by at most a predetermined difference from a value of the measure-ment variable, which can be detected during a previous switch-on phase;

S4) a reference measurement is carried out for detecting a measurement value representing the liquid quality, the measurement value being a reference measurement value;

S5) measurement values are continuously detected, being operating measurement values, using the sensor during further switch-on phases following the defined switch-on phase;

S6) a calculation rule is determined which assigns the comparison measurement value to the reference measurement value; and S7) a final measurement value for measuring the quality is determined from each operating measurement value by means of the calculation rule.

The sensor is thus provided in a step S1 as part of a measuring device for measuring the quality of a liquid and the measuring device is arranged relative to the liquid. The sensor is arranged in the liquid. The part of the measuring device not containing the sensor can be arranged at least partially in the liquid or at a distance from the liquid. For example, the part of the measuring device not containing the sensor is connected to the sensor via an electrically conductive cable. Alternatively, the sensor can be inserted into the measuring device.

In a step S2, the sensor is alternately activated for the duration of a switch-on phase and deactivated for the duration of a switch-off phase. In the activated state, the sensor is supplied with electric power and, in the deactivated state, it is not supplied with electric power. As a result, the sensor is operated in an energy-saving manner and the method is carried out in an energy-saving manner. The duration of the switch-on phase and the duration of the switch-off phase can be set by an operator of the measuring device.

In a step S3, a measurement value is detected as a comparison measurement value by the sensor during a defined switch-on phase. In the defined switch-on phase, the comparison measurement value differs by at most a predetermined difference from a value of the measurement variable that can be detected during a previous switch-on phase. It should be noted that the value of the measurement variable detectable by the sensor, even with a constant measurement variable, changes due to the alternating activation and deactivation of the sensor during the switch-on phases. If, therefore, reference is made in the further course of the description to a detecting of a plurality of measurement values or a comparison of a plurality of measurement values, this is, of course, to be understood as meaning that the measurement values are detected or considered at similar, in particular equal, time intervals from the beginning of the respective switch-on phase in order to obtain correct and comparable measurement results. Thus, for a correct comparison, the comparison measurement value and the value of the measurement variable of a previous switch-on phase are preferably detected or considered at the same time intervals from the beginning of the respective switch-on phase. With regard to the switch-on phase, an operator of the measuring device can determine which switch-on phase is the defined switch-on phase. The comparison measurement value is thus detected at the end or after a transient phase of the alternately activated and deactivated sensor, wherein the values of the measurement variable are then substantially stable at equal intervals from the beginning of the switch-on phases, i.e. differ from one another by no more than the predetermined difference. This transient phase exists when the sensor is alternately activated and deactivated after an extended switch-off phase that was longer than the duration of the switch-off phase, which was required, for example, for maintenance purposes, or after the sensor has been activated for the first time. During the transient phase, the values of the measurement variable will initially differ in several successive switch-on phases and at equal intervals from the beginning of the switch-on phases, but will increasingly approach the comparison measurement value. Thus, in step S3, a comparison measurement value representative of the duration of a switch-on phase of the steady-state sensor is detected.

In a step S4 a reference measurement is carried out for detecting a measurement value which is called a reference measurement value, representing the liquid quality. The reference measurement detects the measurement value with an accuracy that could be achieved, for example, or approximately, also with the sensor if it were permanently activated.

In a step S5, measurement values are continuously detected as operating measurement values using the sensor during further switch-on phases following the defined switch-on phase. The detection of the operating measurement values corresponds to the continuous measurement of a quality of the liquid, in particular water, and is interrupted at the latest by a maintenance activity of an operator of the measuring device, for example for a battery replacement. For a correct measurement, preferably, the operating measurement values are detected at equal intervals from the beginning of the switch-on phases.

In a step S6, a calculation rule is defined, which assigns the comparison measurement value to the reference measurement value. The calculation rule can be determined, for example, in a controller of the measuring device and stored in a memory of the measuring device.

In a step S7, a final measurement value for measuring the quality of the liquid is determined from each operating measurement value by means of the calculation rule. The final measurement value thus represents the quality of the liquid, in particular water.

The method thus provides for the sensor not to be permanently supplied with power as usual, but to be alternately activated and deactivated in order to save energy and to have to replace or recharge energy storage means for power supply as seldom as possible. After a transient phase of the sensor, a comparison measurement value with lower accuracy is detected in a comparatively short switch-on phase and assigned to a reference measurement value with higher accuracy. In continuous measurement operation, operating measurement values are detected with lower accuracy during further comparatively short switch-on phases. Finally, with the aid of the relationship between the comparison measurement value and the reference measurement value, the inaccuracies of the operating measurement values are corrected, whereby final measurement values with higher accuracy are obtained.

According to a preferred embodiment of the method, it is provided that for making the reference measurement S4a) a liquid sample is taken from the liquid and the reference measurement value of the taken liquid sample is detected in a device external to the measuring device; or S4b) the defined switch-on phase or a switch-on phase between the defined switch-on phase and the further switch-on phases for detecting the operating measurement values is extended compared to the preceding switch-on phases, and during the extended switch-on phase the reference measurement value is detected with the sensor.

The reference measurement is thus carried out with higher accuracy compared to the measurement during a switch-on phase. In this case, a reference measurement can be carried out on a liquid sample in an external device using known method steps and using known measuring devices without using the sensor. In this case, the reference measurement is preferably carried out before the determination of the first operating measurement value, for example, before or during the defined switch-on phase of the sensor. Alternatively, the reference measurement can be carried out during an extended switch-on phase with the sensor itself. If the defined switch-on phase is extended for this purpose, the reference measurement is carried out in the defined switch-on phase after the comparison measurement value has been detected.

If the sensor is periodically activated and deactivated at least temporarily, the accuracy of the comparison measurement value and/or of the operating measurement values can be improved. This can be justified by the fact that the measurement values of the sensor can depend not only on the value of the measurement variable itself, but also on the duration of the preceding switch-on phases and switch-off phases. Constantly varying durations of the switch-on phases and switch-off phases can therefore lead to varying measurement values even with a constant value of the measurement variable. Particularly preferably, the sensor is periodically activated and deactivated at least temporarily during ongoing measurement operation, after the defined switch-on phase.

With regard to the defined switch-on phase, it can be provided that

S3a) a switch-on phase is defined as a defined switch-on phase at least when a defined number of previous switch-on phases follow an extended switch-off phase that is longer than the duration of the switch-off phase or follow a first-time activation of the sensor.

The number of preceding switch-on phases can be adjustable. For example, an operator of the measuring device can determine this number based on empirical values. The number of preceding switch-on phases and thus also preceding switch-off phases can be determined in such a way that the sensor is then reliably in the steady state. The specified number of previous switch-on phases is counted from a point in time when the sensor is first switched on or following a longer interruption in the operation of the sensor, i.e. a switch-off phase that is longer than the duration of previous switch-off phases or longer than an average duration of previous switch-off phases. For example, an average switch-off phase can be 20 minutes, while a service interruption can be 1 hour.

With regard to the defined switch-on phase, it can be further provided that

S3b) a switch-on phase is determined at least by the following as a defined switch-on phase:

detecting measurement values with the sensor in several consecutive switch-on phases;

comparing the most recently detected measurement value with the previously detected measurement value; and in the case of a deviation of the two compared measurement values from each other, which deviation falls below a predefined threshold value, determining the switch-on phase for the last measurement value as the defined switch-on phase.

As a result, that switch-on phase can be determined as the defined switch-on phase for which the measurement value differs from the previous measurement value by less than the defined threshold value. The sensor is thus in the steady state. For a correct comparison of the measurement values, the measurement values are preferably detected at the same time intervals from the beginning of the respective switch-on phase.

Furthermore, it is favourable if the comparison measurement value and/or the operating measurement value are detected by measuring the comparison measurement value and/or the operating measurement value at a determined target point in time within the switch-on phase, in particular at the end of the switch-on phase. In this way, particularly reliable measurement results can be achieved, since, as already mentioned above, even with a constant measurement variable, the value of the measurement variable detectable by the sensor changes due to the alternating activation and deactivation of the sensor during the switch-on phases. The target point in time can, for example, be determined and adjustable by an operator of the measuring device. The target point in time can, but does not have to, be at the end of the switch-on phase.

Furthermore, it can be provided that the comparison measurement value and/or the operating measurement value are detected by the following:

measuring with the sensor at several points in time within the switch-on phase associated with the comparison measurement value and/or operating measurement value in order to obtain several sampled values;

calculating a measurement value progression approximated to the sampled values within the switch-on phase;

measuring at what actual point in time the comparison measurement value and/or operating measurement value intended for the measurement at a defined target point in time was actually measured; and in the event of a deviation of the actual point in time from the target point in time, calculating the comparison measurement value and/or operating measurement value at the target point in time by means of the approximated measurement value progression.

In this way, errors in the detection of the comparison measurement value and/or operating measurement value can be corrected, which errors can arise due to the fact that the intended measurement time, i.e. the target point in time, cannot be met. For example, the target point in time cannot be met due to system-related inaccuracies, such as a temporary overload of a processor of the measuring device. From the knowledge of the measurement value progression within the switch-on phase, the measurement value at the intended target point in time can be calculated from the measurement value detected at the actual point in time, preferably by the measuring device itself, in particular by interpolation or extrapolation. In this case, the target point in time can be before or after the actual point in time.

A particularly simple embodiment can provide that the calculation rule is determined as calculating a constant factor, which is formed from the quotient between the comparison measurement value and the reference measurement value, and the final measurement value is determined from each operating measurement value by dividing the operating measurement value by the calculated constant factor.

Accordingly, $$V/R = B/F = Q,$$

$$F = B/Q$$

where V is the comparison measurement value, R is the reference measurement value, B is an operating measurement value, F is a final measurement value, and Q is the constant factor.

The final measurement values calculated by these equations will approximate the actual value of the measurement variable very well, as long as the operating measurement values deviate only slightly from the comparison measurement value. As the deviation increases, for example as a result of a change in the liquid quality, this simple calculation rule becomes more inaccurate due to the non-linear progression of the measurement variable in the switch-on phase.

In order to achieve the most correct final measurement values possible, it is advantageous if S8) the steps S2) to S7) are carried out again if a plurality of operating measurement values compared with one another or a plurality of final measurement values compared with one another deviate from one another by more than a predefined threshold value.

Such a deviation of a plurality of operating measurement values or final measurement values compared with one another is an indication of a changing quality of the liquid. Accordingly, a changed comparison measurement value and a changed reference measurement value can also be expected, which is why steps S2) to S7) of the method are preferably carried out again. The predefined threshold value can be set, for example, by an operator of the measuring device. Preferably, last measured operating measurement values or last calculated final measurement values are compared with longer-standing operating measurement values or final measurement values.

Furthermore, it is preferred that

S9) at least the steps S2), S3) and S5) to S7) are carried out again if the duration of the switch-on phase and/or the duration of the switch-off phase has been changed by more than a predefined threshold value. The change in the duration of the switch-on phase and/or the duration of the switch-off phase can be carried out by an operator of the measuring device, for example, in order to obtain final measurement values at shorter time intervals or to further increase the power saving by the sensor. Since the measurement values that can be detected by the sensor also depend on the duration of the switch-on phase and/or the duration of the switch-off phase, a changed comparison measurement value can also be expected, which is why at least steps S2), S3) and S5) to S7) of the method are preferably carried out again. If the process of the reference measurement is independent of the changed switch-on phases/switch-off phases and thus no new reference measurement value is expected, step S4) of the new reference measurement can also be omitted.

In order to obtain correct final measurement values, it is expedient if steps S2) to S5) are carried out with the same liquid.

In order to achieve correct final measurement values with measuring devices in which a liquid supply to the sensor is carried out by a liquid pump, it is furthermore favourable if S10) a liquid pump of the measuring device, which liquid pump conducts the liquid over the sensor, is already activated before the sensor, for example is activated one minute to two minutes before step S2), in particular is activated before the sensor for a period of time sufficient to supply the liquid to the sensor. This is expedient so that the liquid at the sensor is exchanged in advance and immediately at its switch-on time already represents the liquid that is present at the extraction point, for example in a supply pipe.

It is particularly preferred that the sensor used is a sensor for measuring the concentration of a disinfectant, in particular for measuring a chlorine concentration, or for measuring a pH value. These sensors usually require long activation times, preferably continuous operation, to provide correct measurement results. In addition, these sensors are particularly sensitive at least with regard to changing quality of the liquid, varying durations of the switch-on phase and switch-off phase, the number of previous switch-on phases and switch-off phases, and the residence time in the liquid. With the method according to the invention, final measurement values can also be achieved with such sensors in an energy-saving manner with an accuracy that would not be achievable by shorter switch-on phases alone.

The object stated at the outset is also achieved according to the invention by a measuring device for the energy-saving continuous measurement of a quality of a liquid, in particular of water, comprising at least one sensor, electric power storage means and a controller, which is characterised in that the controller is configured to carry out a method according to the preceding description. The measuring device accordingly comprises at least one sensor with which values of the measurement variable representing the liquid quality, for example a concentration of a disinfectant, a chlorine concentration or a pH value, can be detected. In order to be able to operate the measuring device independently of a power connection, it comprises the electric power storage means. The controller of the measuring device is configured to control the implementation of the method described above. For this purpose, the measuring device preferably comprises a microprocessor and a data memory. With regard to the features of the measuring device, reference is also made to the preceding description of the method, insofar as this is helpful for understanding the measuring device and insofar as features of the measuring device can be derived from this description of the method. Likewise, with regard to the features of the method, reference is also made to the description of the measuring device.

Particularly preferably, the sensor is configured to measure the concentration of a disinfectant, in particular to measure a chlorine concentration, or to measure a pH value.

BRIEF DESCRIPTION OF THE FIGURES

The invention is explained in more detail below with reference to preferred, non-limiting exemplary embodiments and with reference to the drawings. There are shown in.

DETAILED DESCRIPTION

Figure 1:
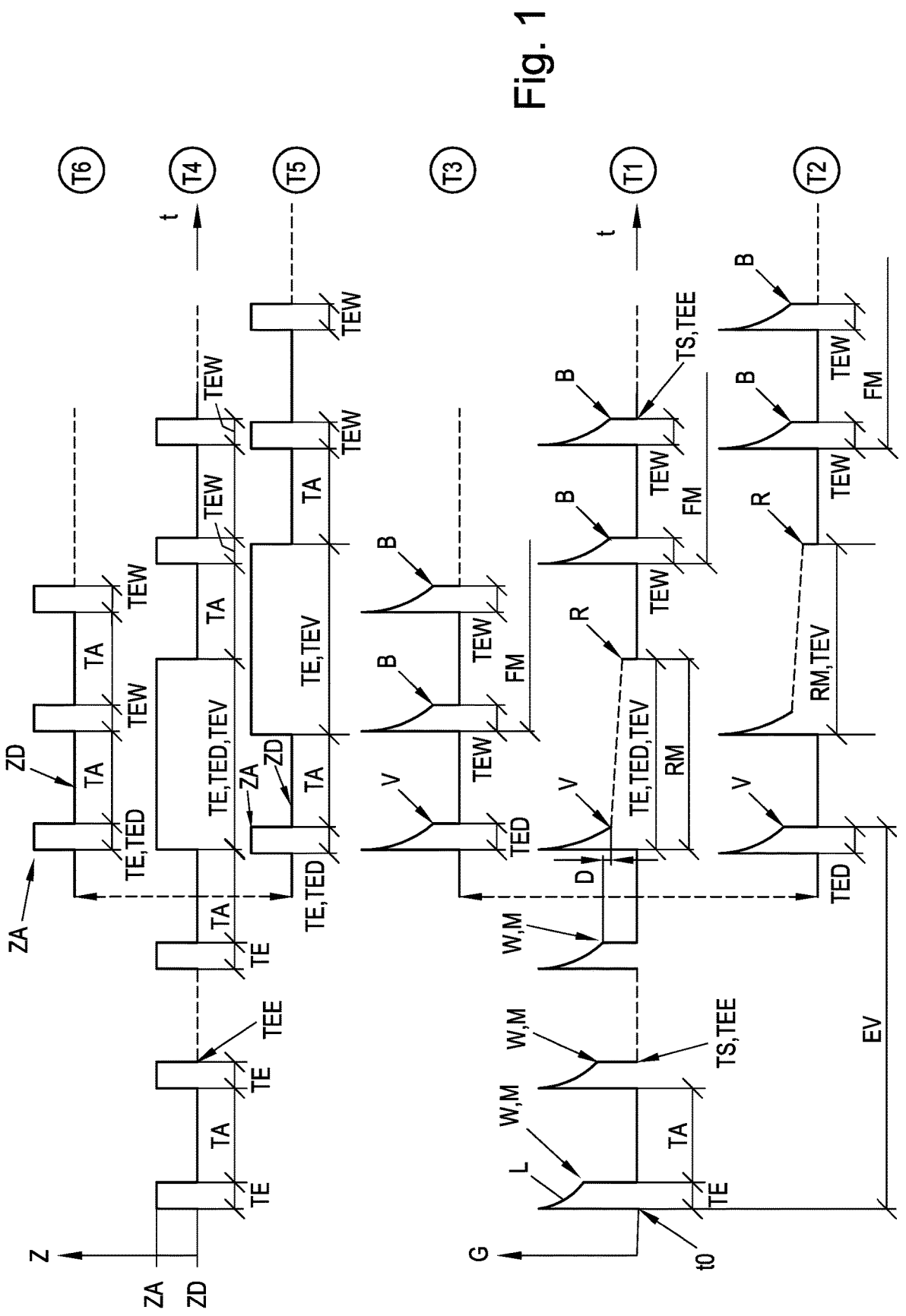
FIG. 1, a schematic representation of a part of the time sequence of the method according to the invention.

FIG. 1 shows, not to scale, a schematic representation of a part of the time sequence of the method for energy-saving continuous measurement FM of a quality of a liquid, in particular water. Before a point in time t0, a sensor 1, which is part of a measuring device 2 and serves to detect a measurement variable G representing the liquid quality, is provided, and the measuring device 2 is arranged relative to the liquid (not shown in FIG. 1). In the example illustrated, the sensor 1 is activated for the first time or after a comparatively long period of time without power at a point in time t0. The sensor 1 can be a sensor 1a to measure the concentration of a disinfectant, in particular to measure a chlorine concentration, or to measure a pH value of the liquid. Following the point in time t0 the sensor 1, 1a is alternately activated for the duration of a switch-on phase TE and deactivated for the duration of a switch-off phase TA. In FIG. 1, a plurality of alternating switch-on phases TE and switch-off phases TA are illustrated. During some switch-on phases TE and switch-off phases TA following the point in time t0, the sensor 1, 1a can settle. The transient phase EV results from the fact that, after its activation (in FIG. 1 at the point in time t0), the sensor 1, 1a must be operated for a long time in comparison to the duration of the switch-on phase TE, for example for a plurality of hours, in order to output correct measurement results. According to the method, however, the sensor 1, 1a is always activated only for the short duration of the switch-on phase TE. In this case, the value W of the measurement variable G, which value W can be detected by the sensor 1, 1a, changes and approaches the correct measurement value, which can only be measured after a correspondingly long time, both within the switch-on phases TE and with each further switch-on phase TE, see the measurement value progression L during a switch-on phase TE and in successive switch-on phases TE in FIG. 1. In FIG. 1, the change in a measurement value M from one switch-on phase TE to the next, in each case at the end of the switch-on phase TE, during the transient phase EV, can be seen. The transient phase EV extends over a plurality of, for example 5 to 10, switch-on phases TE and switch-off phases TA. After the transient phase EV, the same measurement value M can be obtained with the sensor 1, 1a in each switch-on phase TE with the same liquid quality. A defined switch-on phase TED represents the end of the transient phase EV. During the defined switch-on phase TED, a measurement value M is detected as a comparison measurement value V using the sensor 1, 1a, wherein for the defined switch-on phase TED the comparison measurement value V differs by at most a predetermined difference D from a value W of the measurement variable G, which can be detected during a previous switch-on phase TE. With regard to the value W of the measurement variable G, which value W can be detected during a previous switch-on phase TE, it is irrelevant whether the value W is actually detected as the measurement value M. What is important in this context is only that the comparison measurement value V differs at most by the said difference D from a value W of the measurement variable G of a preceding, for example the immediately preceding, switch-on phase TE. This can also be achieved by defining a number of preceding switch-on phases TE and assuming that, after this number of preceding switch-on phases TE, the comparison measurement value V differs by at most the difference D from a value W of the measurement variable G that can be detected during a preceding switch-on phase TE.

FIG. 1 also shows that a reference measurement RM is carried out for detecting a measurement value M, representing the liquid quality, which is referred to as reference measurement value R. The reference measurement RM can be carried out in various ways, which is illustrated in FIG. 1 by splitting the time sequence at the location of the vertical dashed line into three mutually alternative time sequences T1, T2, T3.

The time sequence T1 in FIG. 1 shows an embodiment of the method according to which the defined switch-on phase TED is lengthened compared to the preceding switch-on phases TE and thus represents a lengthened (extended) switch-on phase TEV, during which the reference measurement value R is detected by the sensor 1, 1a. The comparison measurement value V is detected in this extended switch-on phase TEV at the point in time at which it would also be detected if the defined switch-on phase TED were not extended.

The time sequence T2 in FIG. 1 shows an embodiment of the method according to which a switch-on phase TEV is extended between the defined switch-on phase TED and the further switch-on phases TEW, which serve to detect the operating measurement values B. During the extended switch-on phase TEV, the reference measurement value R is detected with the sensor 1, 1a.

The time sequence T3 in FIG. 1 shows an embodiment of the method according to which a liquid sample is taken from the liquid and the reference measurement value R of the taken liquid sample is detected in a device external to the measuring device 2. The taking of the liquid sample, the detection of the reference measurement value R, and the external device are not represented in FIG. 1.

Regardless of how the reference measurement value R is detected, measurement values M are continuously detected as operating measurement values B with the sensor 1, 1a during further switch-on phases TEW, which follow the defined switch-on phase TED, i.e. during the continuous measurement FM. A final measurement value F for measuring the quality is determined from each operating measurement value B by means of a determined calculation rule, the calculation rule assigning the comparison measurement value V to correspond to the reference measurement value R, e.g. by a constant factor Q. The calculation rule can be V/R=Q. With B/F=Q, the final measurement value can be calculated by F=B/Q, where V is the comparison measurement value, R is the reference measurement value, B is an operating measurement value, F is a final measurement value and Q is the constant factor.

FIG. 1 also shows a time sequence of the activation state Z of the sensor 1, 1a, which can be in an activated state ZA and a deactivated state ZD. In this case, the time sequence T4 in FIG. 1 is assigned to the time sequence T1 in FIG. 1, the time sequence T5 in FIG. 1 is assigned to the time sequence T2 in FIG. 1, and the time sequence T6 in FIG. 1 is assigned to the time sequence T3 in FIG. 1.

In FIG. 1, it is further indicated that the sensor 1, 1a is periodically activated and deactivated at least temporarily. The periodic sequence may be subject to slight variations due to limitations in the system, for example a temporary overload of the measuring device, in which case the time sequence is still considered to be periodic. Such acceptable deviations from an exact periodicity can be in the range of a plurality of seconds, for example up to 10 seconds, if, for example, the duration of the switch-on phase TE is between 2 and 4 minutes and the duration of the switch-off phase is between 10 and 20 minutes.

The defined switch-on phase TED can be defined, for example, as that switch-on phase TE which, viewed from the point in time t0, follows a fixed number of preceding switch-on phases TE. In the example according to FIG. 1, this fixed number is at least three. The defined switch-on phase TED can, for example, also be defined as that switch-on phase TE for which a measurement value M detected by the sensor 1, 1a differs from a measurement value M detected in a preceding switch-on phase TE by less than a predefined threshold value D.

In the example represented in FIG. 1, the measurement value M, in particular the comparison measurement value V and/or the operating measurement value B, is detected at the end of the switch-on phases TEE. In general, however, the target point in time TS at which the measurement values M are measured within the switch-on phase TE can be determined in advance and can also deviate from the end of the switch-on phases TEE. For example, the time sequence T1 in FIG. 1 shows a detection of the comparison measurement value V and a detection of the reference measurement value R within the same switch-on phase TE at different points in time.

The switch-on phase TE can be, for example, between 2 and 4 minutes, preferably between 2.5 and 3.5 minutes, in particular 3 minutes. The switch-off phase TA can be, for example, between 10 and 20 minutes, preferably between 13 and 17 minutes, in particular 15 minutes. The extended switch-on phase TEV can extend, for example, over a period of between 1 and 3 hours, preferably between 1.5 and 2.5 hours, in particular 2 hours.

Figures 2, 3, 4, 5:
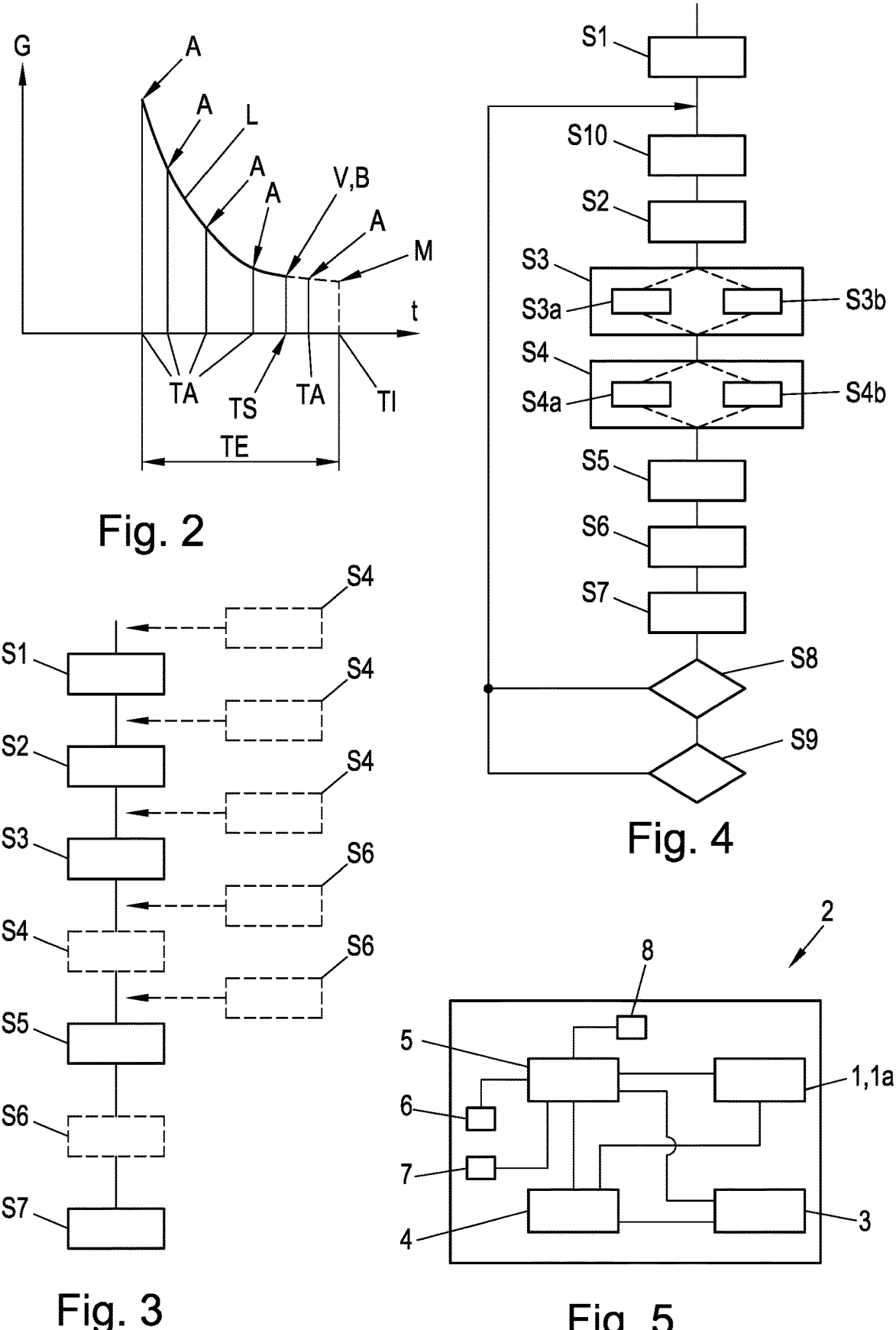
FIG. 2, a schematic representation of the time sequence of a switch-on phase on a larger scale.
FIG. 3, a flowchart for the method according to the invention.
FIG. 4, a more detailed flowchart of the method according to the invention.
FIG. 5, a simplified block diagram of the measuring device according to the invention.

FIG. 2 shows, by way of example, a detection of the comparison measurement value V and/or of an operating measurement value B or, in general, of a measurement value M by means of an approximated measurement value progression L. For this purpose, within the switch-on phase TE in which the comparison measurement value V and/or the operating measurement value B are to be detected, a plurality of measurement values are detected as sampled values A by the sensor 1, la at a plurality of points in time TA. Thereupon, a measurement value progression L approximating the sampled values A is calculated within the switch-on phase TE. The comparison measurement value V and/or operating measurement value B is supposed to be detected at a target point in time TS. The actual point in time TI, at which the comparison measurement value V and/or operating measurement value B was actually detected, is measured. If, undesirably, for example due to overloading of the measuring device, the actual point in time TI deviates from the target point in time TS, the comparison measurement value V and/or operating measurement value B is calculated by means of the approximated measurement value progression L at the target point in time TS. In the example represented in FIG. 2, the measurement was unintentionally delayed, i.e. the target point in time TS is before the actual point in time TI, which is why the measurement value M would be incorrectly detected at the wrong time. To correct the error, the measurement value M can be calculated from the measurement value progression L at the target point in time TS.

FIG. 3 shows a simplified flowchart according to the method. Steps S1 to S7 do not necessarily have to be performed in the order indicated. Rather, a person skilled in the art can determine an expedient order of steps S1 to S7.

In step S1, the sensor 1, 1a is provided as part of a measuring device 2 for measuring the quality of a liquid and the measuring device 2 is arranged relative to the liquid.

In step S2, the sensor 1, 1a is alternately activated for the duration of a switch-on phase TE and deactivated for the duration of a switch-off phase TA. In particular, the sensor 1, 1a can be periodically activated and deactivated at least temporarily.

In step S3, a measurement value M is detected as a comparison measurement value V using the sensor 1, 1a during a defined switch-on phase TED; for which defined switch-on phase TED the comparison measurement value V differs by at most a predetermined difference D from a value W of the measurement variable G, which can be detected during a previous switch-on phase TE.

In step S4 a reference measurement RM is carried out for detecting a measurement value M representing the liquid quality, which is a reference measurement value R. Depending on the type of detection of the reference measurement value M, step S4 can also be carried out earlier, in particular if the reference measurement value M is determined by a liquid sample taken. The possibility of earlier detection is indicated in FIG. 3 by steps S4 represented in dashed lines.

In step S5, measurement values M are continuously detected as operating measurement values B using the sensor 1, 1a during further switch-on phases TEW following the defined switch-on phase TED.

Steps S2 to S5 are preferably carried out with the same liquid.

In step S6, a calculation rule is determined, which assigns the comparison measurement value V to correspond to the reference measurement value R. Step S6 can be carried out as soon as the comparison measurement value V and the reference measurement value R are known, in particular before step S5.

In Step S7 a final measurement value F for measuring the quality is determined from each operating measurement value B by means of the calculation rule.

It is obvious that some steps of the sequence are carried out at the same time. At least steps S3 and S5 to S7 are carried out during the execution of step S2.

FIG. 4 shows a more detailed flowchart according to the method. Also in this example, steps S1 to S10 given do not necessarily have to be carried out in the order indicated. Steps S1 to S7 according to FIG. 4 correspond to steps S1 to S7 according to FIG. 3 and will therefore not be described again in connection with FIG. 4.

Step S3 may comprise a step S3a or a step S3b. In step S3a, a switch-on phase TE is defined as the defined switch-on phase TED when a fixed number of previous switch-on phases TE follow an extended switch-off phase TA that is longer than the duration of the switch-off phase TA or follow a first-time activation of the sensor 1, 1a. In step S3b, a switch-on phase TE is defined at least by the following as the defined switch-on phase TED: Measurement values M are detected with the sensor 1, 1a in a plurality of successive switch-on phases TE. The most recently detected measurement value M is compared with the previously detected measurement value M. If the deviation of the two compared measurement values M from one another falls below a predefined threshold value, the switch-on phase TE for the last measurement value M is determined as the defined switch-on phase TED. In addition, the defined switch-on phase TED can also be determined in another way.

Step S4 may comprise a step S4a or a step S4b. In step S4a, a liquid sample is taken from the liquid and the reference measurement value R of the taken liquid sample is detected in a device external to the measuring device 2. In step S4b, the defined switch-on phase TED is extended or a switch-on phase TEV between the defined switch-on phase TED and the further switch-on phases TEW, which serve to detect the operating measurement values B, is extended. During the extended switch-on phase TEV, the reference measurement value R is detected with the sensor 1, 1a.

In steps S3 and/or S5, furthermore, it can also be provided that the comparison measurement value V and/or the operating measurement value B are detected by measuring the comparison measurement value V and/or the operating measurement value B at a determined target point in time TS within the switch-on phase TE, in particular at the end of the switch-on phase TEE.

Furthermore, in steps S3 and/or S5, it can be provided that the comparison measurement value V and/or the operating measurement value B are detected by the following: measuring with the sensor 1, 1a at a plurality of points in time TA within the switch-on phase TE associated with the comparison measurement value V and/or operating measurement value B in order to obtain a plurality of sampled values A; calculating a measurement value progression L approximated to the sampled values A within the switch-on phase TE; measuring at which actual point in time TI the comparison measurement value V and/or operating measurement value B intended for the measurement at a defined target point in time TS has actually been measured; and in the event of a deviation of the actual point in time TI from the target point in time TS, calculating the comparison measurement value V and/or operating measurement value B at the target point in time TS by means of the approximated measurement value progression L.

In step S6, it can also be provided that the calculation rule is determined as calculating a constant factor Q, which is formed from the quotient between the comparison measurement value V and the reference measurement value R.

In step S7, it can also be provided that the final measurement value F is determined from each operating measurement value B by dividing the operating measurement value B by the calculated constant factor Q.

In step S8, steps S2 to S7 are carried out again if a plurality of operating measurement values B compared with one another or a plurality of final measurement values F compared with one another deviate from one another by more than a predefined threshold value.

In step S9, at least steps S2, S3 and S5 to S7 are carried out again if the duration of the switch-on phase TE and/or the duration of the switch-off phase TA has been changed by more than a predefined threshold value.

In step S10, a liquid pump 3 of the measuring device 2, which liquid pump 3 conducts the liquid over the sensor 1, 1a, is already activated before the sensor (1, 1a), for example is activated one minute to two minutes before step S2), in particular is activated before the sensor (1, 1a) for a period of time sufficient to supply the liquid to the sensor (1, 1a).

FIG. 5 shows a simplified block diagram of a measuring device 2 for the energy-saving continuous measurement FM of a quality of a liquid, in particular of water. The measuring device 2 comprises at least one sensor 1, 1a, electric power storage means 4, and a controller 5. The controller 5 is configured to carry out or control the method. In addition, a liquid pump 3 may be provided. The controller 5 is connected to the sensor 1, 1a, the electric power storage means 4 and the liquid pump 3. In addition, the electric power storage means 4 is connected to the sensor 1, 1a and the liquid pump 3. The measuring device 2 can also comprise a data memory 8, an input device 6 for inputting parameters, for example a reference value R, and an output device 7 at least for the final measurement values F. In addition, the output device 7 can output a notification if a plurality of operating measurement values B compared with one another or a plurality of final measurement values F compared with one another deviate from one another by more than a predefined threshold value.

The invention claimed is:

1. A method for energy-saving, continuous measuring of a quality of a liquid using a measuring device having a sensor for detecting a measurement variable in the liquid, wherein:

S1) the measuring device is arranged relative to the liquid and the sensor detects the measurement variable in the liquid;

S2) the sensor is alternatingly activated for a duration of a switch-on phase and deactivated for a duration of a switch-off phase;

S3) a switch-on phase in a steady state of the sensor is defined as a defined switch-on phase and a measurement value is detected as a comparison measurement value by the sensor during the defined switch-on phase when a value of the measurement variable differs by at most a predetermined difference from a value of the measurement variable during a previous switch-on phase;

S4) a reference measurement is carried out to detect a reference measurement value representing a reference quality of the liquid;

S5) during further switch-on phases following the defined switch-on phase, the sensor continuously detects measurement values in the liquid as operating measurement values representing operating qualities of the liquid;

S6) a calculation rule assigns the comparison measurement value to correspond to the reference measurement value; and S7) a final measurement value representing a final quality of the liquid is determined based on the calculation rule and each of the operating measurement values; wherein in order to carry out the reference measurement S4b) the defined switch-on phase or a switch-on phase between the defined switch-on phase and the further switch-on phases for detecting the operating measurement values is extended compared to the preceding switch-on phases, and during the extended switch-on phase the reference measurement value is detected using the sensor.

2. The method according to claim 1, wherein the sensor is periodically activated and deactivated at least temporarily.

3. The method according to claim 1, wherein

S3a) a switch-on phase is defined as the defined switch-on phase at least when a determined number of previous switch-on phases follow an extended switch-off phase that is longer than the duration of the switch-off phase or follow a first-time activation of the sensor.

4. The method according to claim 1, wherein

S3b) a switch-on phase is defined at least by the following as the defined switch-on phase:

detecting measurement values with the sensor in a plurality of consecutive switch-on phases;

comparing the most recently detected measurement value with the previously detected measurement value; and in the case of a deviation of the two compared measurement values from each other which deviation falls below a predefined threshold value, defining the switch-on phase for the last measurement value as the defined switch-on phase.

5. The method according to claim 1, wherein the comparison measurement value and/or the operating measurement value are detected by measuring the comparison measurement value and/or the operating measurement value at a determined target point in time within the switch-on phase.

6. The method according to claim 5, wherein the determined target point is an end of the switch-on phase.

7. The method according to claim 1, wherein the comparison measurement value and/or the operating measurement value are detected by:

measuring with the sensor at a plurality of points in time within the switch-on phase associated with the comparison measurement value and/or operating measurement value in order to obtain a plurality of sampled values;

calculating a measurement value progression approximated to the sampled values within the switch-on phase;

measuring at what actual point in time the comparison measurement value and/or operating measurement value intended for the measurement at a defined target point in time was actually measured; and in the event of a deviation of the actual point in time from the target point in time, calculating the comparison measurement value and/or operating measurement value at the target point in time by means of the approximated measurement value progression.

8. The method according to claim 1, wherein the calculation rule assigns the comparison measurement value to correspond to the reference measurement value so as to determine a constant factor, which is formed from a quotient between the comparison measurement value and the reference measurement value, and the final measurement value is determined for each of the operating measurement values by dividing each of the operating measurement values by the calculated constant factor.

9. The method according to claim 1, wherein

S8) the steps S2) to S7) are carried out again if a plurality of operating measurement values compared with one another or a plurality of final measurement values compared with one another deviate from one another by more than a predefined threshold value.

10. The method according to claim 1, wherein

S9) at least the steps S2), S3) and S5) to S7) are carried out again if the duration of the switch-on phase and/or the duration of the switch-off phase has been changed by more than a predefined threshold value.

11. The method according to claim 1, wherein

S10) a liquid pump of the measuring device, which liquid pump conducts the liquid over the sensor, is already activated before the sensor, for example, is activated one minute to two minutes before step S2), and is activated before the sensor for a period of time sufficient to supply the liquid to the sensor.

12. The method according to claim 1, wherein a sensor for measuring the concentration of a disinfectant, for measuring a chlorine concentration, or for measuring a pH value, is used as the sensor.

13. A measuring device for the energy-saving continuous measurement of a quality of a liquid comprising at least one sensor, an electric power storage means and a controller, wherein the controller is configured to carry out a method according to claim 1.

14. The measuring device according to claim 13, wherein the sensor is configured to measure the concentration of a disinfectant, to measure a chlorine concentration, or to measure a pH value.

\* \* \* \* \*